United States Patent
Leeson et al.

(10) Patent No.: US 9,939,806 B2
(45) Date of Patent: Apr. 10, 2018

(54) DENTAL MILLING SYSTEM

(71) Applicant: James R. Glidewell Dental Ceramics, Inc., Newport Beach, CA (US)

(72) Inventors: David Christopher Leeson, Tustin, CA (US); Michael John Selberis, Ladera Ranch, CA (US); Vaheh Golestanian Nemagrdi, Orange, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 316 days.

(21) Appl. No.: 14/674,629

(22) Filed: Mar. 31, 2015

(65) Prior Publication Data

US 2016/0291585 A1    Oct. 6, 2016

(51) Int. Cl.
| | | |
|---|---|---|
| *G05B 19/18* | (2006.01) |
| *G05B 19/418* | (2006.01) |
| *G05B 19/4093* | (2006.01) |
| *A61C 13/00* | (2006.01) |
| *A61C 5/77* | (2017.01) |

(52) U.S. Cl.
CPC .......... *G05B 19/40937* (2013.01); *A61C 5/77* (2017.02); *A61C 13/0004* (2013.01); *G05B 2219/36283* (2013.01); *G05B 2219/36294* (2013.01); *G05B 2219/45167* (2013.01)

(58) Field of Classification Search
CPC .................. A61C 13/0004; A61C 5/77; G05B 19/40937; G05B 2219/36283; G05B 2219/36294; G05B 2219/45167
See application file for complete search history.

(56) References Cited

U.S. PATENT DOCUMENTS

| | | | |
|---|---|---|---|
| 5,027,509 A | 7/1991 | Barben et al. | |
| 5,684,708 A | 11/1997 | Kondou et al. | |
| 6,970,760 B2 * | 11/2005 | Wolf .................. | A61C 13/0004 433/213 |
| 7,112,065 B2 * | 9/2006 | Kopelman ......... | A61C 13/0004 433/213 |
| 7,178,731 B2 | 2/2007 | Basler | |
| 7,234,938 B2 | 6/2007 | Bodenmiller | |
| 7,708,560 B2 | 5/2010 | Kraemer et al. | |
| 7,774,080 B2 | 8/2010 | Holzner et al. | |
| 8,348,669 B1 | 1/2013 | Schmitt | |

(Continued)

*Primary Examiner* — Abdelmoniem Elamin
(74) *Attorney, Agent, or Firm* — Charles C. Fowler (57) ABSTRACT

Systems and methods are provided for machining dental prostheses including, over a network, receiving data concerning a dental prosthesis, selecting a material from which to machine the dental prosthesis, and determining machining instructions for machining the dental prosthesis based on a nominal enlargement factor corresponding to the selected material. The method can also include storing the machining instructions, receiving a request from a milling machine for a dental prosthesis to be milled by the milling machine, and associating the dental prosthesis with the milling machine. The method can also include selecting a material blank comprised of the selected material, determining a material blank enlargement factor of the selected material blank, modifying the machining instructions according to a difference between the nominal enlargement factor and the material blank enlargement factor, and machining the dental prosthesis according to the modified machining instructions.

10 Claims, 6 Drawing Sheets

(56) References Cited

U.S. PATENT DOCUMENTS

| | | | |
|---|---|---|---|
| 8,401,690 B2 | 3/2013 | Gleditzsch et al. | |
| 8,568,897 B2 | 10/2013 | Ganley et al. | |
| 2004/0158342 A1* | 8/2004 | Wolf | A61C 13/0004 700/98 |
| 2005/0261795 A1* | 11/2005 | Ghosh | A61C 13/0004 700/118 |
| 2006/0115794 A1 | 6/2006 | Sager | |
| 2006/0204932 A1 | 9/2006 | Haymann et al. | |
| 2007/0190402 A1 | 8/2007 | Kumeuchi et al. | |
| 2007/0190481 A1 | 8/2007 | Schmitt | |
| 2008/0085489 A1 | 4/2008 | Schmitt | |
| 2011/0066267 A1 | 3/2011 | Schmitt | |
| 2011/0136080 A1 | 6/2011 | Holzner et al. | |
| 2011/0171604 A1* | 7/2011 | Durbin | A61C 9/0053 433/213 |
| 2011/0313547 A1* | 12/2011 | Hernandez | G05B 19/042 700/23 |
| 2013/0170378 A1* | 7/2013 | Ray | G01S 5/0289 370/252 |
| 2015/0142513 A1* | 5/2015 | Shnayder | G06Q 30/0272 705/7.31 |

\* cited by examiner

DENTAL MILLING SYSTEM

FIELD

The present disclosure relates to systems and methods of manufacturing dental prostheses.

BACKGROUND

Dental prostheses are typically manufactured at specialized dental laboratories that employ computer-aided design (CAD) and computer-aided manufacturing (CAM) milling systems to produce dental prostheses according to patient-specific specifications provided by dentists. In a typical work flow, information about the oral situation of a patient is received from a dentist, the dental laboratory designs the dental prosthesis, and the prosthesis is assigned to a block of material, or material blank, having size, shape, color, and material-type properties suitable for creating the prosthesis. The material blank is generally a pre-sintered ceramic, and is associated with unique predetermined shrinkage information corresponding to a factor by which the material blank will shrink when fully sintered. Many conventional dental milling systems then determine numerical code for machining the dental prosthesis that accounts for the unique shrinkage information associated with the assigned material blank, thereby tying the production of the dental prosthesis to the assigned material blank. Thus, a given dental prosthesis cannot be manufactured until the specified material blank is placed in a milling machine, which can slow production of dental prostheses, and reduce system resiliency to equipment failure. Accordingly, improvements to dental milling systems are desirable.

SUMMARY

Certain embodiments of the disclosure concern systems and methods for machining dental prostheses including, over a network, receiving data concerning a dental prosthesis, selecting a material from which to machine the dental prosthesis, and determining machining instructions for machining the dental prosthesis based on a nominal enlargement factor corresponding to the selected material. The method can further comprise storing the machining instructions, receiving a request from a milling machine for a dental prosthesis to be milled by the milling machine, and associating the dental prosthesis with the milling machine. The method can further comprise selecting a material blank comprised of the selected material, determining a material blank actual enlargement factor of the selected material blank, modifying the machining instructions according to a difference between the nominal enlargement factor and the material blank actual enlargement factor, and machining the dental prosthesis according to the modified machining instructions.

In another representative embodiment, a system comprises a dental prosthesis database to, over a network, receive and store data concerning a dental prosthesis, and a machining instructions tool to determine machining instructions for machining the dental prosthesis based at least in part on the data concerning the dental prosthesis and a nominal enlargement factor. The system further includes a dental prosthesis selection module to associate the machining instructions with a milling machine based on a request from the milling machine for a dental prosthesis to be milled by the milling machine, and a controller to select a material blank, determine a material blank actual enlargement factor of the selected material blank, and modify the machining instructions according to a difference between the nominal enlargement factor and the material blank actual enlargement factor. The milling machine can be communication with the controller, and can be configured to receive the modified machining instructions and to machine the dental prosthesis according to the modified machining instructions.

Another representative embodiment includes one or more non-transitory computer-readable media storing computer executable instructions for causing a computer to perform a method, the method comprising over a network, receiving data concerning a dental prosthesis, selecting a material from which to machine the dental prosthesis, and determining machining instructions for machining the dental prosthesis based on a nominal enlargement factor corresponding to the selected material. The method can further comprise storing the machining instructions, receiving a request from a milling machine for a dental prosthesis to be milled by the milling machine, associating the dental prosthesis with the milling machine, selecting a material blank comprised of the selected material, and determining a material blank actual enlargement factor of the selected material blank. The method can further comprise modifying the machining instructions according to a difference between the nominal enlargement factor and the material blank actual enlargement factor, and machining the dental prosthesis according to the modified machining instructions.

The foregoing and other objects, features, and advantages of the disclosed embodiments will become more apparent from the following detailed description, which proceeds with reference to the accompanying figures.

DETAILED DESCRIPTION

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In some examples, values, procedures, or apparatus may be referred to as "lowest," "best," "minimum," or the like. It will be appreciated that such descriptions are intended to indicate that a selection among many alternatives can be made, and such selections need not be better, smaller, or otherwise preferable to other selections.

In the following description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

Example 1—Representative Dental Milling System

In a conventional dental milling system workflow, information used to design and manufacture a dental prosthesis for a patient is received from a dentist or dental office. In some representative examples, a dentist or dental office will provide information concerning the oral situation of a patient, such as a physical impression or an electronic file containing a digital scan of the patient's oral situation. Additionally, the dentist or dental office may also provide instructions for the material or materials to be used to manufacture the prosthesis, the type and construction of the prosthesis, the shade or other aesthetic features for the prosthesis, and the like. As used herein, the term "dental prosthesis" refers to any dental restorative including, without limitation, crowns, bridges, dentures, partial dentures, implants, onlays, inlays, or veneers, to name a few. Using the foregoing information, a dental laboratory will design a dental restoration, typically using a design software package such as FastDesign™ dental design software available from IOS Technologies, Inc. of San Diego, Calif. CAD/CAM machining instructions (also referred to as "numerical code" or "NC code") are determined based upon the type of restoration, the digital design of the dental prosthesis, and the selected material, and a material blank or ingot comprised of the specified material is placed into a milling machine, which mills (i.e., "machines") the dental prosthesis from the material blank according to the machining instructions. The milled prosthesis is then removed from the milling machine for further processing consistent with the type of material or prosthesis (e.g., sintering, polishing, etc.), and the final dental prosthesis is packaged for delivery to the dentist.

Typically, the material blanks comprise a ceramic material, and are in a pre-sintered or partially sintered state such that the material blanks can be easily milled by the milling machine. After milling, the resulting pre-sintered or partially sintered dental prostheses can be colored with various pigments to match the shade of the patient's natural dentition, and then fully sintered to harden the dental prostheses. In other embodiments, the material blanks are formed of a material that includes coloring agents to match or approximate the shade of the patient's natural dentition, or any other desired shade. The final sintering process can cause the pre-sintered or partially sintered dental prostheses to experience a dimensional reduction, or shrink. The amount of shrinkage that a ceramic material will undergo during final sintering is often unique to each material blank, and may be expressed as a ratio $D_0/D_F$, where $D_0$ is an initial dimension of the material blank prior to final sintering and $D_F$ is a final dimension of the material blank after final sintering (see, e.g., FIG. 6). The ratio $D_0/D_F$ can define an enlargement factor of the material blank, which may be predetermined based upon batch material properties and diagnostic measurements of the individual material blank. In some embodiments, an enlargement factor may be derived theoretically based upon the material used in the blank and its properties. In other embodiments, an enlargement factor is determined via measurements (e.g., physical dimensions, displacement, weight) of the actual material blank. In some examples, the enlargement factor of a material blank may range in value from about 1.1 to about 1.3, depending upon the type of ceramic material.

In some exemplary embodiments, an enlargement factor is determined based upon volumetric measurements. Because the target densities of many sintered ceramic materials (e.g., zirconia) are known, the amount of shrinkage that occurs during sintering may be predicted very accurately. For example, the size of a milling blank may be measured using a coordinate measuring machine (CMM) or other device to obtain a volume of the blank, and its weight may be measured. From these measurements, the density of the pre-sintered or partially sintered milling blank may be ascertained. The enlargement factor for the milling blank is then calculated as the cube root of the ratio of the target density to the (measured) pre-sintered or partially sintered density:

$$EF = \sqrt[3]{\frac{\rho \text{ (fully densified)}}{\rho \text{ (pre-sintered)}}}$$

Depending upon the material used to manufacture the material blank, the manufacturing method, or other factors, the material blank may be either isotropic or it may be anisotropic, e.g., having different shrinkage characteristics along different axes of the blank. For example, a material blank that is manufactured using an isostatic pressing method may have shrinkage characteristics that are different from a blank that is manufactured using biaxial or uni-axial pressing. In some cases, therefore, a material blank may possess an enlargement factor in its XY orientation that is different from the enlargement factor in the Z direction (directions being expressed using a conventional Cartesian coordinate system that is recognized by those skilled in the art). The dental milling systems and methods described herein are adapted for and are suitable for use with either isotropic or anisotropic dental material blanks.

In order for a dental prosthesis to achieve the desired size and shape after final sintering, the machining instructions for machining the dental prosthesis must account for the unique enlargement factor of the material blank from which the dental prosthesis will be milled. This can be done by, for example, increasing the dimensions of the dental prosthesis when initially milled from the partially sintered material blank by a factor equal to the enlargement factor of the material blank. In other words, oversizing the dental prosthesis according to the enlargement factor of the material blank from which the dental prosthesis is machined can help to ensure that the dental prosthesis shrinks to the desired size after final sintering.

Figure 1:
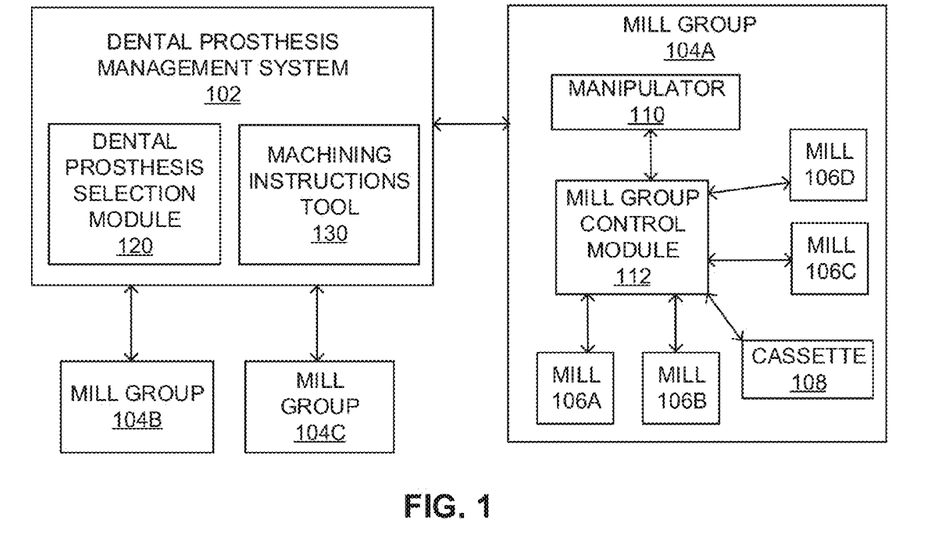
FIG. 1 is a schematic illustration of a representative embodiment of a dental milling system.

FIG. 1 is a schematic illustration of a representative embodiment of a dental milling system 100 including a dental prosthesis management system 102 and a plurality of mill groups 104A-104C. The dental prosthesis management system 102 can include a dental prosthesis selection module 120 and a machining instructions tool 130, and can be in communication with each of the mill groups 104A-104C such that it can coordinate the operation of the mill groups to produce dental prostheses, as further described below.

Figure 2:
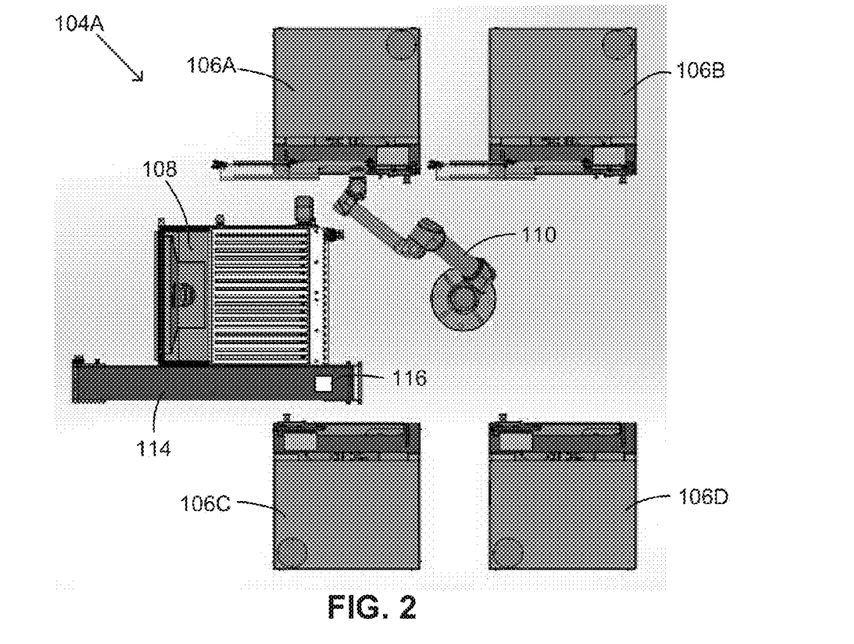
FIG. 2 is a plan view of a physical implementation of a mill group of the dental milling system of FIG. 1.

Each of the mill groups 104A-104C can include one or more mills, a manipulator, a material blank cassette (also referred to as a "tray" or "rack"), and a mill group control module (also referred to as a "controller"). For example, FIG. 2 illustrates an exemplary mill group 104A including four milling machines 106A-106D (also referred to as "mills"), a material blank cassette 108, a manipulator 110, and a mill group control module 112 that coordinates the operation of the mills 106A-106D with the cassette 108 and the manipulator 110.

Figures 3, 4, 5, 6:
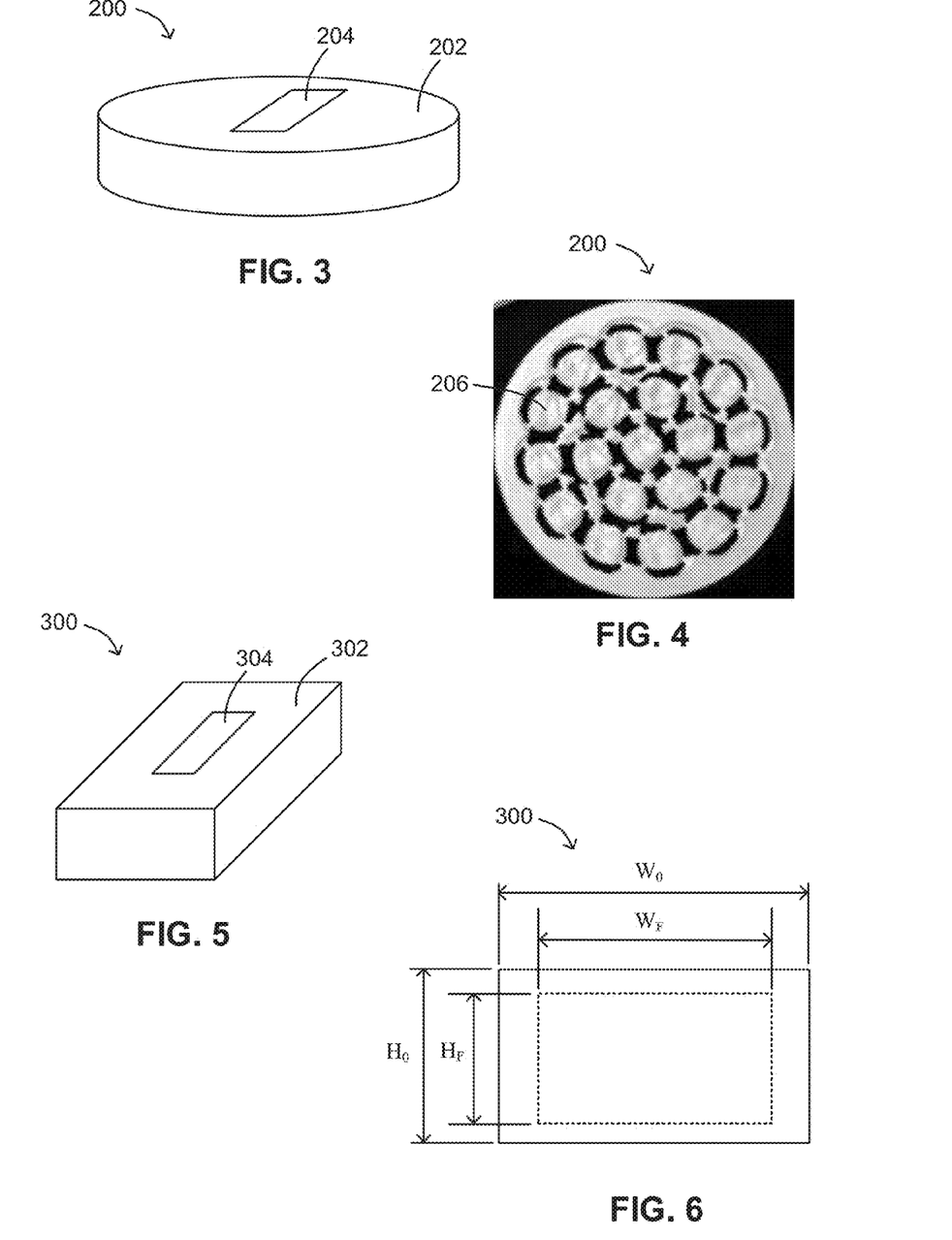
FIG. 3 illustrates a representative embodiment of a disk-shaped material blank.
FIG. 4 is a plan view of the material blank of FIG. 3 illustrating a plurality of dental prostheses milled into the material blank.
FIG. 5 illustrates a representative embodiment of a rectangularly-shaped material blank.
FIG. 6 is a cross-sectional view of the material blank of FIG. 5 illustrating representative height and width dimensions prior to and after final sintering.

Referring to FIGS. 3-6, the cassette 108 (FIGS. 1 and 2) can include a plurality of material blanks such as representative material blank 200 illustrated in FIGS. 3 and 4, and/or representative material blank 300 illustrated in FIGS. 5 and 6. The material blank 200 of FIG. 3 can have a disk-shaped body 202, and can have a diameter and thickness suitable for machining a plurality of dental prostheses 206 from a single material blank, as shown in FIG. 4. The material blank 300 of FIG. 5 can have an elongated body 302 and a rectangular cross section, as shown in FIG. 6. Although representative disk-shaped and elongated-shaped material blank bodies are illustrated in the figures, in other embodiments, the material blank has other geometric or non-geometric shapes or forms, provided that the size and shape of the blank is sufficient to produce the desired dental prosthesis. In some embodiments, the material blank 300 can be suitable for milling a single dental prosthesis (e.g., a crown), or a small number of dental prostheses, depending upon the size of the material blank and the dental prosthesis or prostheses to be milled.

Referring to the material blank 300 for purposes of illustration, FIG. 6 schematically illustrates the relative size of a cross-section of the material blank 300 when partially sintered (indicated in solid lines) and after final sintering (indicated in phantom). The initial and final heights of the material blank 300 are illustrated by dimensions $H_O$ and $H_F$, and the initial and final widths are illustrated by dimensions $W_O$ and $W_F$. As described above the, ratios $H_O/H_F$ and $W_O/W_F$ can determine the material blank enlargement factor of the material blank 300, which must be accounted for when determining the machining instructions for machining a dental prosthesis to help ensure that the dental prosthesis achieves the desired size after machining and final sintering.

Referring again to FIGS. 3 and 5, the material blanks 200, 300 can include respective barcodes 204, 304, which can include information regarding the material blanks 200, 300, such as the enlargement factors of the respective material blanks 200, 300. In some embodiments, the material blanks 200, 300 can comprise any biocompatible ceramic, including silica-, alumina-, leucite-, and/or zirconia-based ceramics, or any combination thereof. In one representative embodiment, the material blanks 200, 300 can be made from Prismatik Clinical Zirconia™ available from Glidewell Laboratories. The material blanks 200, 300 can also be of any suitable shape, size, and/or color shade, and the cassette 108 can include a plurality of examples of material blanks having any such shape, size, and/or color shade combination, as desired.

In the exemplary embodiment of FIGS. 1 and 2, the control module 112, in response to instructions from the dental prosthesis management system 102, can cause the manipulator 110 to pick a material blank from the cassette 108 and place it into one of the mills 106A-106D for milling by the mill. In some embodiments, the manipulator 110 can be a robotic arm, as shown in FIG. 2. In some embodiments, the manipulator 110 and/or the mill into which the material blank is placed can include a barcode reader or other device to scan the barcode associated with the material blank, and can transmit information concerning the material blank to the dental prosthesis management system 102. The milling machine can then machine a dental prosthesis, shown schematically at 116, according to machining instructions provided by the machining instructions tool 130. After milling, the manipulator 110 can remove the milled dental prosthesis 116 from the mill and place it, for example, on a conveyor 114, which can convey the dental prosthesis 116 away from the mill group 104A for further processing. The manipulator 110 can load material blanks into the various mills 106A-106D and unload milled dental prostheses from the mills 106A-106D as instructions are received from the dental prosthesis management system 102.

Although three mill groups 104A-104C are illustrated in FIG. 1, it should be understood that the milling system 100 can include any suitable number of mill groups. Further, the mill groups can include any suitable number of mills, manipulators, cassettes, and/or controllers, as desired. It should also be understood that the mills such as mills 106A-106D need not be grouped into mill groups, but may be arranged in any suitable arrangement, including a plurality of discrete mills, or a single mill, and may be located locally or remotely (for example, chair-side in a dental office) with respect to the dental prosthesis management system 102, as desired. Additionally, the mills 106A-106D, the cassette 108, and the manipulator 110 of each of the mill groups 104A-104C can include their own internal controller(s), memory, and processors to execute instructions received from the respective mill group control modules, such as control module 112, and/or from the dental prosthesis management system 102.

Example 2—Representative Dental Prosthesis Management System

Figure 7:
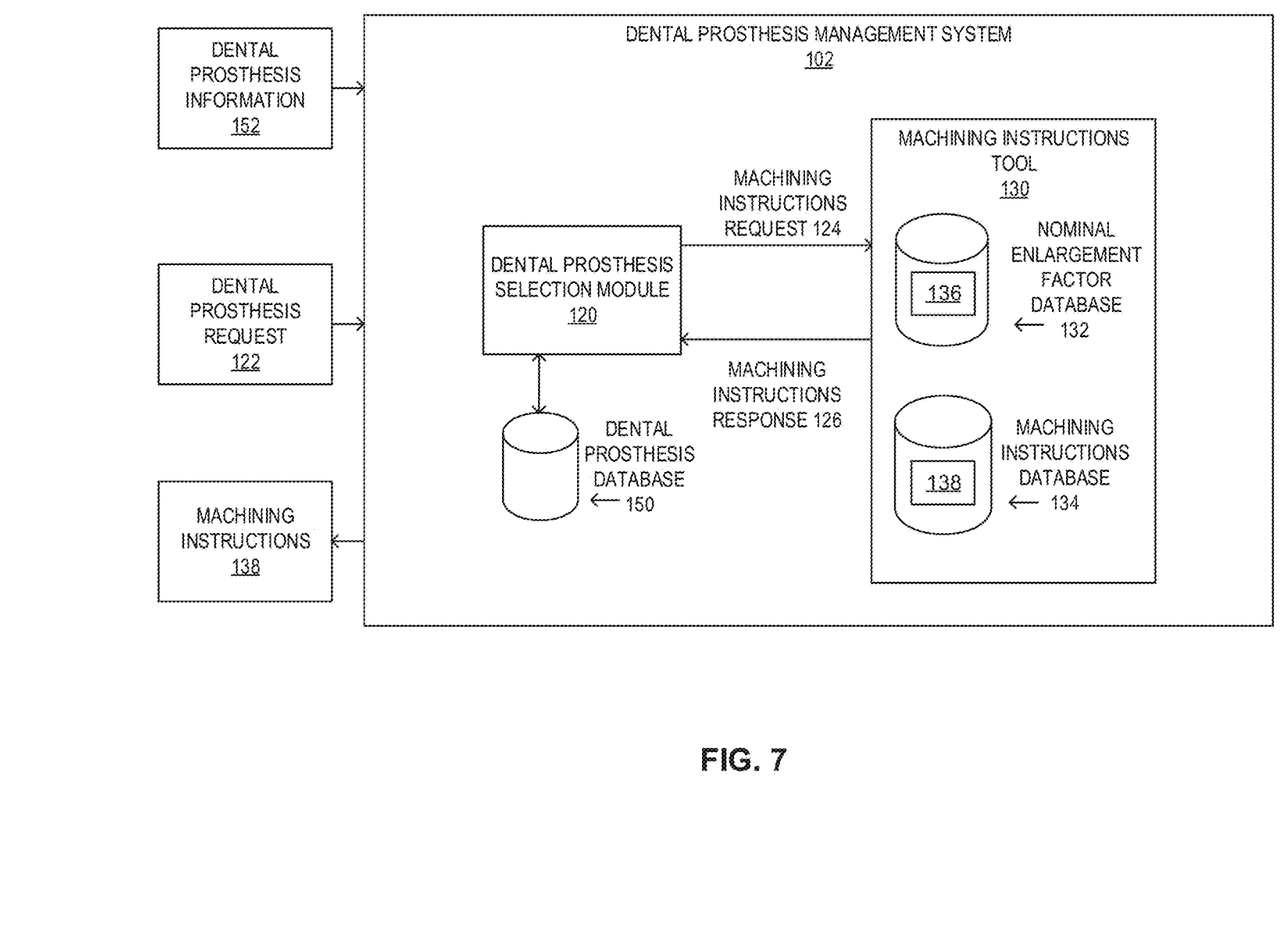
FIG. 7 is a schematic illustration of a representative embodiment of a dental prosthesis management system.

The dental prosthesis management system 102 can be any system capable of performing tasks related to the manufacture of dental prostheses, and can be implemented on a computer system, such as a server. Referring to FIG. 7, the dental prosthesis management system 102 can include the dental prosthesis selection module 120, the machining instructions tool 130, and a dental prosthesis database 150. The machining instructions tool 130, in turn, can include a nominal enlargement factor database 132 and a machining instructions database 134. The databases 150, and 134 can be internal to the dental prosthesis management system 102, located on an external device connected to the dental prosthesis management system 102, or located remotely, such as in cloud-based storage.

In practice, the systems shown herein, such as the dental prosthesis management system 102 can vary in complexity, with different functionality, components of differing complexity, and the like. Further, although a single instance is shown, a large number of instances, some sharing data, databases, configuration information, and the like, can be supported. Also, the dental prosthesis management system 102 can comprise a variety of other functionality not shown to address synchronization, security, load balancing, multi-tenancy, redundancy, and the like.

Although various components of the systems herein are shown as a single component, in practice, the boundaries between components can be changed. For example, although the system is shown as executing on a single server, in practice, functionality can be implemented across one or more machines, virtual or physical.

The dental prosthesis management system 102, any of the other systems described herein, and subsets of such systems can be implemented in conjunction with any of the hardware components described herein, such as the described computing systems (e.g., processing units, memory, and the like). In any of the examples herein, the inputs, outputs, databases, documents, and the like can be stored in one or more computer-readable storage media or computer-readable storage devices. The technologies described herein can be generic to the specifics of operating systems or hardware and can be applied in any variety of environments to take advantage of the described features.

As illustrated in FIG. 7, the nominal enlargement factor database 132 can include nominal enlargement factors 136 corresponding to the different material types from which material blanks in the various cassettes, such as cassette 108, are comprised. The nominal enlargement factors 136 can be, for example, average values of the enlargement factors corresponding to the respective material types. For example, for a zirconia-based ceramic having an enlargement factor typically ranging from about 1.21 to about 1.24, the nominal enlargement factor 136 for that zirconia-based ceramic can be about 1.225. The nominal enlargement factor database 132 can store a plurality of nominal enlargement factors 136 corresponding to a plurality of materials, and the nominal enlargement factors 136 can be periodically updated as necessary to reflect different materials or material properties as, for example, new material blanks are received by the dental milling system 100.

As described in more detail below, a "nominal enlargement factor" 136 is a value that is used to generate an initial set of machining instructions 138 for machining a given dental prosthesis 116 from a material blank. The initial set of machining instructions 138 that are generated using the nominal enlargement factor 136 are later adjusted (via a correction factor) to account for the difference between the nominal enlargement factor 136 and the actual enlargement factor for the material blank being used to generate the dental prosthesis 116. In some embodiments, the nominal enlargement factor 136 may be derived empirically (e.g., as an average or mean value of a number of examples), or it may be a theoretical value derived from the properties of the material used in the material blank, or it may be selected based upon other criteria.

The dental prosthesis management system 102 can receive dental prosthesis information 152 associated with a dental prosthesis 116 to be milled by the dental milling system 100, which can be used to create one or more entries in the dental prosthesis database 150. In some embodiments, the dental prosthesis database 150 can be implemented as a queue or a first-in-first-out data structure, in which dental prostheses 116 are selected for milling in the order in which their associated dental prosthesis information 152 was received by the dental milling system 100. Other implementations are possible, including a structure in which dental prosthesis information 152 concerning certain dental prostheses 116 can be weighted or prioritized such that dental prostheses 116 selected for machining are not necessarily selected in the order in which they were received (to allow prioritization of rush orders, for example).

The dental prosthesis information 152 can be passed to the machining instructions tool 130, which can select the material type from which the dental prosthesis is to be manufactured (based on, for example, a material specified by the dentist or determined according to the type, size, etc., of the dental prosthesis), and retrieve a nominal enlargement factor 136 for that material type from the nominal enlargement factor database 132. The machining instructions tool 130 can then determine machining instructions 138 (for example, numerical code) for machining the dental prosthesis 116 according to the nominal enlargement factor 136, and store the machining instructions 138 in the machining instructions database 134.

For purposes of illustration, the following description proceeds with respect to mill 106A of mill group 104A of FIGS. 1 and 2. However, it should be understood that the following description is applicable to any of the mills and/or mill groups described herein. When mill 106A is available for a new dental prosthesis milling job, the control module 112 can transmit a dental prosthesis request 122, which can be received by the dental prosthesis management system 102. The dental prosthesis selection module 120 can then query the dental prosthesis database 150 concerning dental prosthesis information 152 for a dental prosthesis to be milled by the mill 106A. The dental prosthesis database 150 can identify the dental prosthesis 116 as the next dental prosthesis to be milled. The dental prosthesis selection module 120 can then send a machining instructions request 124 to the machining instructions tool 130 requesting the machining instructions 138 associated with the dental prosthesis 116. The machining instructions tool 130 can retrieve the appropriate machining instructions 138 from the machining instructions database 134, and provide the machining instructions 138 to the dental prosthesis selection module 120 in a machining instructions response 126. The dental prosthesis management system 102 can then transmit the machining instructions 138 to the mill group control module 112. In some embodiments, the machining instructions 138 can include information indicative of the nominal enlargement factor 136 upon which the machining instructions 138 are based.

Figure 8:
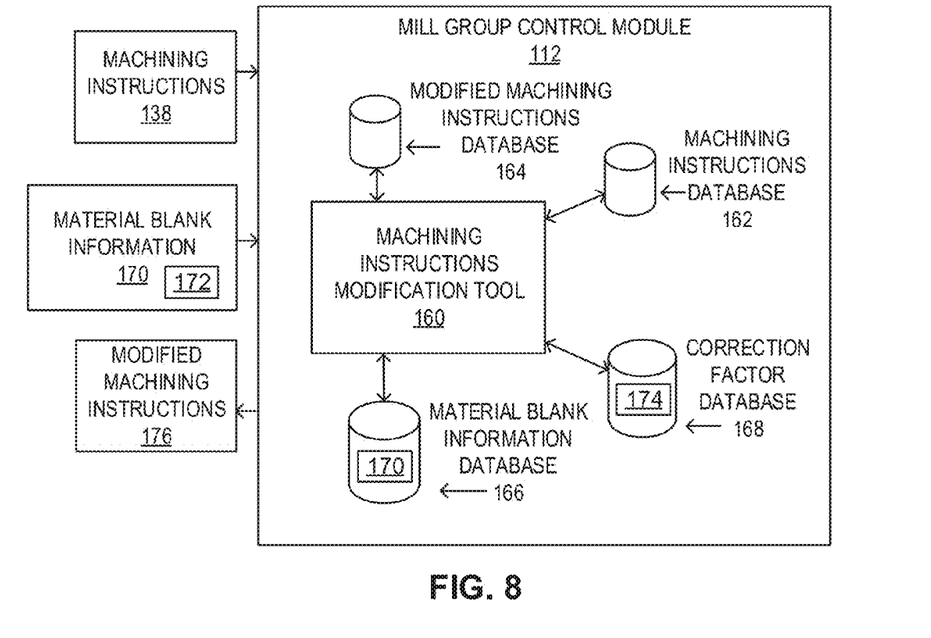
FIG. 8 is a schematic illustration of a representative embodiment of a mill group control module.

FIG. 8 schematically illustrates a representative embodiment of the mill group control module 112. The control module 112 can include a machining instructions modification tool 160, a machining instructions database 162, a modified machining instructions database 164, a material blank information database 166, and a correction factor database 168. Additionally, although the mill group control module 112 is shown as a separate entity from the mills 106A-106D, it should be understood that any of the disclosed functionality can also be carried out by, for example, one or more discrete controllers (and/or other associated hardware or software features) associated with each individual milling machine 106A-106D.

The control module 112 can receive the machining instructions 138 associated with the dental prosthesis 116 and information of the nominal enlargement factor 136, which can be stored in the machining instructions database 162. The control module 112 can then transmit control signals for causing the manipulator 110 to select a material blank from the cassette 108, obtain material blank information 170 (by, for example, scanning a barcode associated with the material blank), and place the material blank in the mill 106A. In some embodiments, the material blank information 170 can include data concerning identification of the material blank and the material blank actual enlargement factor, as further described below with respect to FIG. 10. In some embodiments, the material blank can also be selected based at least in part on, for example, a size of the material blank, a shade of the material blank, and/or the type of prosthesis being manufactured (e.g., a posterior crown, an anterior crown, a posterior bridge, an anterior bridge, an inlay, an onlay, or the like), as desired.

The material blank information 170 can be returned to the control module 112 and stored as one or more entries in the material blank information database 166. In some embodiments, certain of the material blank information, such as the material blank actual enlargement factor, can be initially stored in the material blank information database 166 when, for example, the material blank is initially inventoried, and subsequently retrieved from the material blank information database 166 when the corresponding material blank is selected for milling a dental prosthesis. In alternative embodiments, the material blank information database 166 can be associated with the dental prosthesis management system 102, and the material blank information 170 can be transmitted to the dental prosthesis management system 102 for storage.

In some embodiments, the material blank information 170 can include a material blank actual enlargement factor 172 specifying an enlargement factor value specific to the particular material blank associated with the material blank information 170. The machining instructions modification tool 160 can then determine a correction factor 174, which can be given by the expression below. The correction factor 174 can represent a difference between the nominal enlargement factor 136 used to determine the machining instructions 138 and the material blank actual enlargement factor 172, and can be stored in the correction factor database 168.

Correction Factor=1−(Nominal $EF$−Material Blank Actual $EF$)

Using the correction factor 174, the machining instructions modification tool 160 can determine modified machining instructions 176 (for example, by altering the tool path of a milling tool) based at least in part on the machining instructions 138 and the correction factor 174. In this manner, the modified machining instructions tool 160 can account for the difference between the nominal enlargement factor 136 and the material blank actual enlargement factor 172. The modified machining instructions 176 can then be stored in the modified machining instructions database 164, and/or transmitted to the mill 106A, which can mill the dental prosthesis 116 from the material blank according to the modified machining instructions 176. For example, in some embodiments, the modified machining instructions 176 are not stored in the modified machining instructions database 164. Rather, the machining instructions 138 are modified line by line by scaling each command by the correction factor 174 as each command is processed in order to generate the modified machining instructions 176.

As noted previously, in some embodiments a material blank may possess an enlargement factor in its XY orientation that is different from the enlargement factor in the Z direction. In these embodiments, the correction factor 174 will include components that account for the difference by having different values depending upon the orientation of the machining instructions command. The modified machining instructions tool 160 applies the appropriate correction factor 174 component to each command as the modified machining instructions 176 are generated.

For example, for a representative dental prosthesis to be milled from a zirconia-based ceramic, machining instructions 138 can be determined by the machining instructions tool 130 according to a nominal enlargement factor of 1.225, as described above. When the machining instructions 138 are provided to a mill group control module, such as control module 112, in response to a request for a dental prosthesis to be milled, the control module 112 can obtain the material blank enlargement factor 172 corresponding to the material blank from which the dental prosthesis will be milled (e.g., by causing a barcode reader to scan the barcode associated with the material blank). The control module 112 can then determine the correction factor 174 based on the material blank actual enlargement factor 172. For example, if the selected material blank has an associated material blank enlargement factor 172 of 1.230, then the correction factor 174 can be determined to be about 1.005. Using the correction factor 174, the machining instructions modification tool 160 can then modify the machining instructions 138 based at least in part on the correction factor 174, and store the modified machining instructions 176 in the modified machining instructions database 164 and/or provide the modified machining instructions 176 to the mill 106A.

Those skilled in the art will recognize that a relatively larger correction factor 174 can potentially lead to a larger degree of error in the modified machining instructions 176 relative to a situation in which the machining instructions are originally created based upon the material blank actual enlargement factor 172. As a result, it is advantageous to have a correction factor 174 having a value as close as possible to 1.000. It follows that it is advantageous to have a nominal enlargement factor 136 that is as close as possible to the material blank actual enlargement factor 172. This error reduction also demonstrates at least one reason why it is advantageous to provide a nominal enlargement factor 136 in the process of generating the initial machining instructions 138, rather than generating the instructions using a 1:1 scale with the resulting relatively larger correction factor 174.

The manufacturing systems and methods described herein provide the ability to generate an initial set of machining instructions 138 that are based upon the dental prosthesis information 152 prior to the time that the machining instructions 138 are associated with a specific material blank. This allows the dental milling system 100 to mill dental prostheses with any available milling machine using any material blank available to that machine because the machining instructions for machining the dental prostheses can be determined independent of the specific material blanks from which the dental prostheses will be milled. Thus, unlike conventional dental milling systems, which determine the machining instructions for a given dental prosthesis according to an enlargement factor for a particular material blank, this can provide the ability to assign dental prosthesis milling jobs to mills and/or mill groups on an as-requested basis without regard to whether a particular material blank is available for use by that mill or mill group (i.e., located in a cassette associated with that mill or mill group). In other words, by determining the machining instructions 138 according to a nominal enlargement factor 136 and modifying the machining instructions according to a material blank enlargement factor 172 associated with a particular material blank only after that material blank is selected for milling the dental prosthesis, dental prosthesis milling jobs can be distributed to any available milling machine in the system at any time. This can speed the production of dental prostheses because any dental prosthesis can be milled by any mill using any material blank. This can also provide flexibility and resiliency to equipment failures because, for example, if one or more milling machines (or manipulators, controllers, etc.) fail prior to or during milling of a dental prosthesis, the milling job can be easily routed to a second mill or mill group, and the machining instructions for that dental prosthesis can be modified according to an enlargement factor of another material blank available for use by that mill or mill group with minimal human intervention.

Example 3—Dental Prosthesis Database

Figure 9:
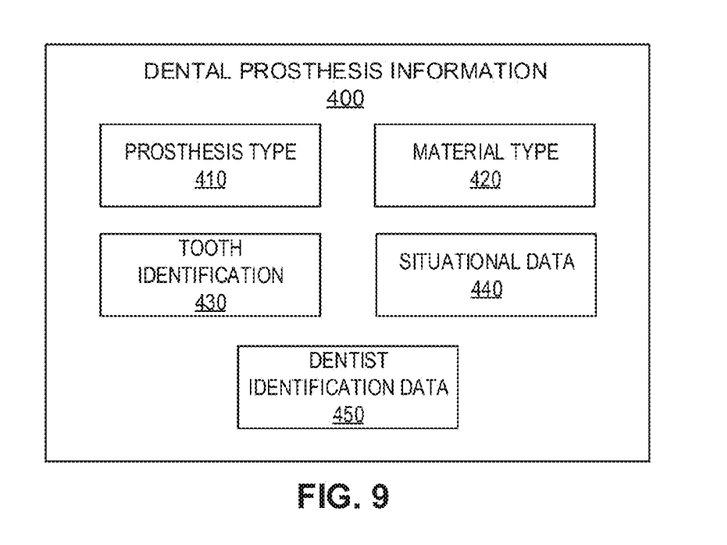
FIG. 9 is a block diagram illustrating exemplary dental prosthesis information.

FIG. 9 illustrates exemplary dental prosthesis information 400 for a dental prosthesis to be milled by the dental milling system 100. The dental prosthesis information 400 can be provided to the dental prosthesis management system 102 as dental prosthesis information 152 and stored as an entry in the dental prosthesis database 150.

The dental prosthesis information 400 can include such information as the type of dental prosthesis 410 to be manufactured (e.g., crown, implant, bridge, etc.), a material type 420 from which the dental prosthesis is to be manufactured, an identification 430 of the tooth or portion of a tooth to be prosthetically recreated, and situational data 440 concerning the position of the dental prosthesis in a patient's mouth (e.g., data concerning a dental impression, or photographic data). In addition, the dental prosthesis information 400 can include the design information created for the design of the dental prosthesis 410 to be manufactured, such as design information created using a dental CAD software program. In some embodiments, the dental prosthesis information 400 can also include identification information 450 concerning a dentist or dental office requesting manufacture of the dental prosthesis, and/or patient identification information.

Example 4—Material Blank Database

Figure 10:
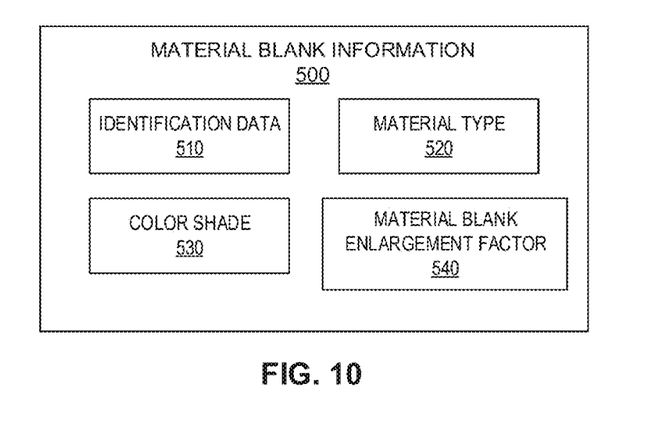
FIG. 10 is a block diagram illustrating exemplary material blank information.

FIG. 10 illustrates exemplary material blank information 500 for a material blank, such as the material blanks 200, 300 described above. The material blank information 500 can be stored on one or more barcodes associated with each material blank, such as barcodes 204, 304 of the material blanks 200, 300, and can be provided to the dental prosthesis management system 102 as material blank information 170 and stored as an entry in the material blank information database 166.

The material blank information 500 can include such information as identification data 510 (for example, a serial number), the type of material 520 from which the material blank is made, a color shade identifier 530 identifying a color shade of the material blank, and a material blank enlargement factor 540 of the material blank. In addition, the material blank information 500 can also include information such as the size, shape, or other physical characteristics of the material blank.

Example 5—Exemplary Method of Machining a Dental Prosthesis

Figure 11:
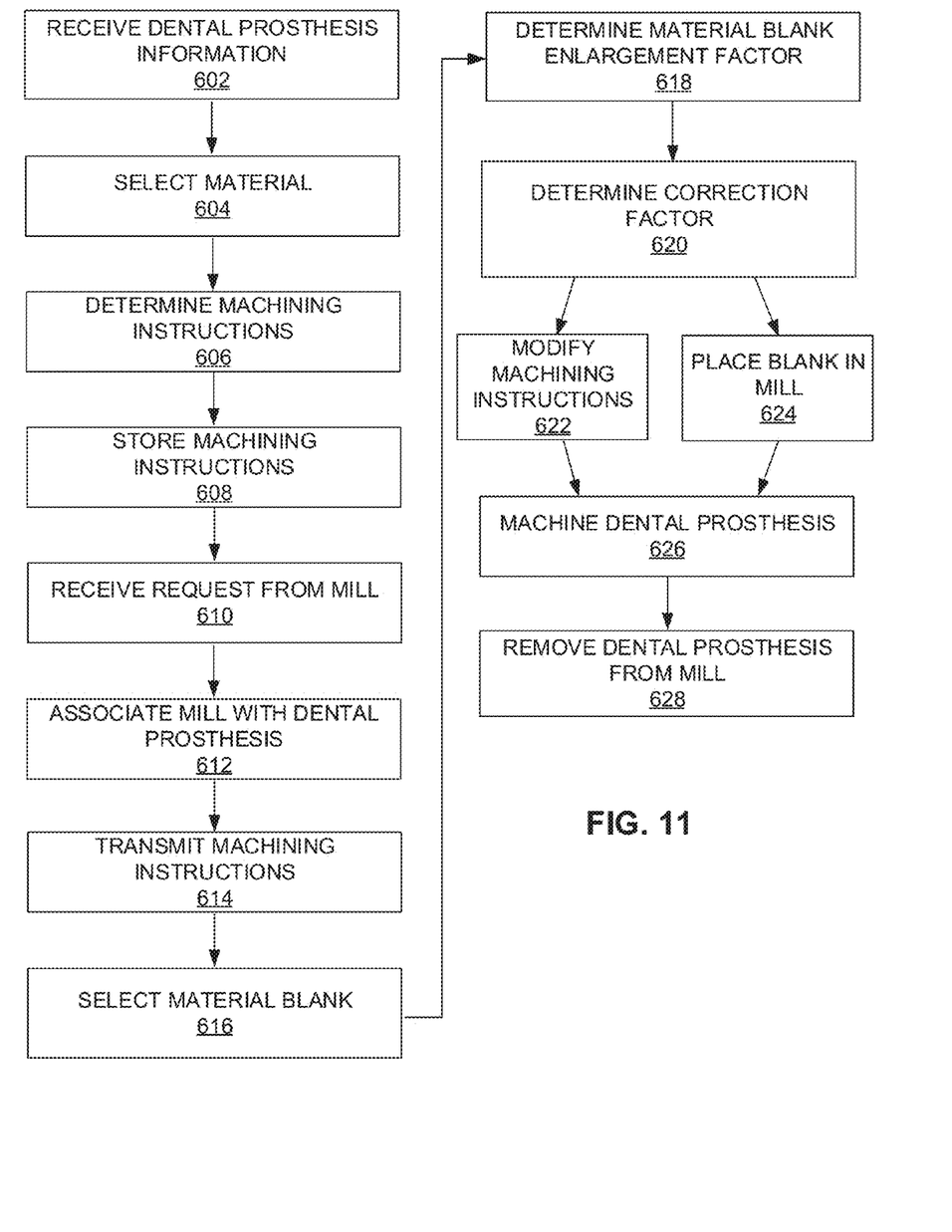
FIG. 11 is a schematic block diagram illustrating a representative method of milling a dental prosthesis.

FIG. 11 is a schematic block diagram illustrating a representative method of milling a dental prosthesis. At process block 602, the dental milling system 100 can receive dental prosthesis information for a new dental prosthesis to be milled, which can be stored in a database, such as the dental prosthesis database 150 of FIG. 7. Based at least in part on the dental prosthesis information, a material from which to machine the dental prosthesis can be selected at process block 604. At process block 606, machining instructions for machining the dental prosthesis can be determined based at least in part on the dental prosthesis information and a nominal enlargement factor corresponding to the selected material. At process block 608, the machining instructions can be stored in, for example, the machining instructions database 134 of FIG. 7.

At process block 610, the dental milling system 100 can receive a request from a mill or a mill group control module for a dental prosthesis to be milled by the mill or mill group. At process block 612, the dental prosthesis can be associated with the mill or mill group. At process block 614, the machining instructions associated with the dental prosthesis can be transmitted to the mill or mill group control module. In some embodiments, the machining instructions can include information of the nominal enlargement factor used to determine the machining instructions. At process block 616, a material blank can be selected from which to mill the dental prosthesis, and a material blank actual enlargement factor of the selected material blank can be obtained from the material blank at process block 618. Using the material blank actual enlargement factor, a correction factor can be determined at block 620. The machining instructions can then be modified according to the correction factor (i.e., according to a difference between the nominal enlargement factor and the material blank actual enlargement factor) at block 622 to determine modified machining instructions, and the material blank can be placed in the appropriate mill at block 624. The dental prosthesis can then be milled according to the modified machining instructions at block 626. At block 628, the milled dental prosthesis can be removed from the mill and made available for further processing.

Example 6—Exemplary Computing Environment

Figure 12:
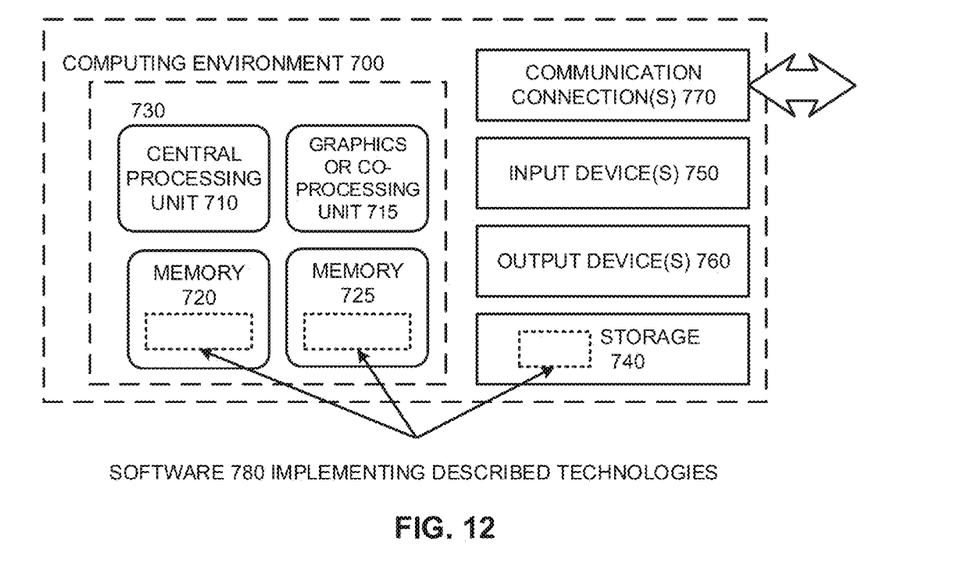
FIG. 12 is a schematic illustration of a representative computing environment in which described embodiments, techniques, and technologies can be implemented.

FIG. 12 depicts a generalized example of a suitable computing environment 700 in which the described innovations may be implemented. The computing environment 700 is not intended to suggest any limitation as to scope of use or functionality, as the innovations may be implemented in diverse general-purpose or special-purpose computing systems. For example, the computing environment 700 can be any of a variety of computing devices (e.g., desktop computer, laptop computer, server computer, tablet computer, gaming system, mobile device, programmable automation controller, etc.) that can be incorporated into a computing system comprising one or more computing devices.

With reference to FIG. 12, the computing environment 700 includes one or more processing units 710, 715 and memory 720, 725. In FIG. 12, this basic configuration 730 is included within a dashed line. The processing units 710, 715 execute computer-executable instructions. A processing unit can be a central processing unit (CPU), a processor in an application-specific integrated circuit (ASIC), or any other type of processor. In a multi-processing system, multiple processing units execute computer-executable instructions to increase processing power. For example, FIG. 12 shows a central processing unit 710 as well as a graphics processing unit or co-processing unit 715. The tangible memory 720, 725 may be volatile memory (e.g., registers, cache, RAM), non-volatile memory (e.g., ROM, EEPROM, flash memory, etc.), or some combination of the two, accessible by the processing unit(s). The memory 720, 725 stores software 780 implementing one or more innovations described herein, in the form of computer-executable instructions suitable for execution by the processing unit(s).

A computing system may have additional features. For example, in some embodiments, the computing environment 700 includes storage 740, one or more input devices 750, one or more output devices 760, and one or more communication connections 770. An interconnection mechanism (not shown) such as a bus, controller, or network, interconnects the components of the computing environment 700. Typically, operating system software (not shown) provides an operating environment for other software executing in the computing environment 700, and coordinates activities of the components of the computing environment 700.

The tangible storage 740 may be removable or non-removable, and includes magnetic or optical media such as magnetic disks, magnetic tapes or cassettes, CD-ROMs, DVDs, or any other medium that can be used to store information in a non-transitory way and can be accessed within the computing environment 700. The storage 740 stores instructions for the software 780 implementing one or more innovations described herein.

The input device(s) 750 may be, for example: a touch input device, such as a keyboard, mouse, pen, or trackball; a voice input device; a scanning device; any of various sensors; another device that provides input to the computing environment 700; or combinations thereof. For video encoding, the input device(s) 750 may be a camera, video card, TV tuner card, or similar device that accepts video input in analog or digital form, or a CD-ROM or CD-RW that reads video samples into the computing environment 700. The output device(s) 760 may be a display, printer, speaker, CD-writer, or another device that provides output from the computing environment 700.

The communication connection(s) 770 enable communication over a communication medium to another computing entity. The communication medium conveys information, such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

Any of the disclosed methods can be implemented as computer-executable instructions stored on one or more computer-readable storage media (e.g., one or more optical media discs, volatile memory components (such as DRAM or SRAM), or nonvolatile memory components (such as flash memory or hard drives)) and executed on a computer (e.g., any commercially available computer, including smart phones, other mobile devices that include computing hardware, or programmable automation controllers) (e.g., the computer-executable instructions cause one or more processors of a computer system to perform the method). The term computer-readable storage media does not include communication connections, such as signals and carrier waves. Any of the computer-executable instructions for implementing the disclosed techniques as well as any data created and used during implementation of the disclosed embodiments can be stored on one or more computer-readable storage media. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, JavaScript, Adobe Flash, or any other suitable programming language. Likewise, the disclosed technology is not limited to any particular computer or type of hardware. Certain details of suitable computers and hardware are well known and need not be set forth in detail in this disclosure.

It should also be well understood that any functionality described herein can be performed, at least in part, by one or more hardware logic components, instead of software. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

In view of the many possible embodiments to which the principles of the disclosure may be applied, it should be recognized that the illustrated embodiments are only preferred examples and should not be taken as limiting the scope of the disclosure. Rather, the scope of the invention is defined by all that comes within the scope and spirit of the following claims.

What is claimed is:

1. A system for fabricating a dental prosthesis from a material blank, comprising:
    a dental prosthesis database to, over a network, receive and store data concerning a dental prosthesis;
    a machining instructions tool to determine machining instructions for machining the dental prosthesis based at least in part on the data concerning the dental prosthesis and a nominal enlargement factor;
    a dental prosthesis selection module to associate the machining instructions with a milling machine based on a request from the milling machine for a dental prosthesis to be milled by the milling machine; and
    a controller to select a material blank, determine a material blank enlargement factor of the selected material blank, and modify the machining instructions according to a difference between the nominal enlargement factor and the material blank enlargement factor;
    wherein the milling machine is in communication with the controller, and is configured to receive the modified machining instructions and to machine the dental prosthesis according to the modified machining instructions.

2. The system of claim 1, wherein:
    the milling machine further comprises a plurality of milling machines and a manipulator; and
    wherein the controller is configured to cause the manipulator to select the material blank and to place the material blank in one of the plurality of milling machines.

3. The system of claim 1, wherein the milling machine is configured to modify the machining instructions according to the difference between the nominal enlargement factor and the material blank enlargement factor.

4. The system of claim 1, wherein the machining instructions tool is configured to modify the machining instructions according to the difference between the nominal enlargement factor and the material blank enlargement factor.

5. The system of claim 1, further comprising a barcode scanner to scan a barcode associated with the selected material blank to determine the material blank enlargement factor.

6. The system of claim 1, wherein the machining instructions tool is configured to select a material from which to machine the dental prosthesis based at least in part on the data concerning the dental prosthesis.

7. The system of claim 3, wherein the milling machine is configured to modify a milling tool path according to the difference between the nominal enlargement factor and the material blank enlargement factor.

8. The system of claim 4, wherein the machining instructions tool is configured to modify a milling tool path according to the difference between the nominal enlargement factor and the material blank enlargement factor.

9. The system of claim 1, further comprising a material blank database from which information concerning the material blank is retrieved.

10. The system of claim 1, wherein:
    the data concerning the dental prosthesis includes color shade data; and
    the controller selects the material blank based at least in part on the color shade data.

* * * * *